United States Patent [19]
Heller et al.

[11] Patent Number: 5,665,222
[45] Date of Patent: Sep. 9, 1997

[54] SOYBEAN PEROXIDASE ELECTROCHEMICAL SENSOR

[75] Inventors: Adam Heller, Austin, Tex.; Mark S. Vreeke, Boulder, Colo.

[73] Assignee: E. Heller & Company, Alameda, Calif.

[21] Appl. No.: 540,789

[22] Filed: Oct. 11, 1995

[51] Int. Cl.[6] .................. G01N 27/26; G01N 27/327
[52] U.S. Cl. .................. 205/792; 205/777.5; 204/403; 435/817
[58] Field of Search ..................... 435/11, 14, 28, 435/817, 6; 204/403; 205/777.5, 792

[56] References Cited

U.S. PATENT DOCUMENTS

| | | | |
|---|---|---|---|
| 4,840,893 | 6/1989 | Hill et al. | 435/6 |
| 5,278,046 | 1/1994 | Johnson et al. | 435/7.9 |
| 5,320,725 | 6/1994 | Gregg et al. | |

FOREIGN PATENT DOCUMENTS

| | | |
|---|---|---|
| 62-155099 | 7/1987 | Japan . |
| 02087056 | 3/1990 | Japan . |
| 02268684 | 11/1990 | Japan . |
| 9320230 | 10/1993 | WIPO . |

OTHER PUBLICATIONS

Csoregi et al. (Anal. Chem. 1994, 66, 3131–3138; "Design, Characterization, and One–Point in Vivo Calibration of a Subcutaneously Implanted Glucose Electrode"). Oct. 1, 1994.
JAPIO abstract of JP 02087056 (Teruaki et al.) Mar. 27, 1990.
WPIDS (Derwent) abstract of WO 9320230 (Bannister et al.). Oct. 14, 1993.
JAPIO abstract of JP 62155099 (Yoshitsugu et al.). Jul. 10, 1987.
JAPIO abstract of JP 02268684 (Hirosuke et al.). Nov. 2, 1990.
Alvarez–Icaza, et al., *Anal. Chem.*, 65:525A–533A (1993).
Asther, et al., *Appl. Biochem. Biotechnol.*, 38:57–67 (1993).
Chien, et al., *Biotechnol. Appl. Biochem.*, 19:51–60 (1994).
Darnell, et al., *Molecular Cell Biology*, Scientific American Books, Inc., New York (1986) month is currently unavailable.
Enzymol International, Inc. 2543 Westbelt Dr., Columbus, OH 43228, Product Literature.
Gorton, et al., *Anal. Chim. Acta*, 250:203–248 (1991).
Gregg, et al., *J. Phys. Chem.*, 95:5970–5975 (1991) month is currently unavailable.
Kallury, et al., *Anal. Chem.*, 64:1062–1068 (1992).
Kallury, et al. *Anal. Chem.*, 65:2459–2467 (1993).
Katakis, et al., *J. Am. Chem. Soc.*, 116:3617–3618 (1994).
Kulys, et al., *Bioelectrodchem. Bioenerg.*, 24:305–311 (1990).
McNeil, et al., *Anal. Chem.*, 61:25–29 (1989).
Paddock, et al., *J. Electoanal. Chem. Interfacial Electrochem.*, 260:487–494 (1989).
Ryan, et al., *Enzyme Microb. Technol.*, vol. 16:501–505 (Jun. 1994).
Tatsuma, et al., *Anal. Chem.*, 61:2352–2355 (1989).
Vreeke, et al., *Anal. Chem.*, 64:3084–3090 (1992) month currently available.
Vreeke, et al., *In Diagnostic Biosensor Polymers*, ACS Symposium Series 556:180–193 (1994).
Wang, et al. *Anal. Chim. Acta*, 254:81–88 (1991).
Yang, et al., *Analytical Chemistry*, 67:1326–1331 (1995).

*Primary Examiner*—T. Tung
*Assistant Examiner*—Alex Noguerola
*Attorney, Agent, or Firm*—Merchant & Gould, Smith, Edell, Welter & Schmidt, P.A.

[57] ABSTRACT

An electrochemical biosensor able to measure hydrogen peroxide which is stable at temperatures near 37° C. or in excess of 37° C. for sustained periods of time and in biological environments. The electrochemical biosensor contains a thermostable peroxidase, preferably derived from soybean, and is useful in analytical biosensors.

19 Claims, 1 Drawing Sheet

□ SBP — periodate/Schiff base crosslinked
◇ SBP — PEGDE crosslinked
○ HRP — periodate/Schiff base crosslinked
△ HRP — PEGDE crosslinked □  SBP — periodate/Schiff base crosslinked
◇  SBP — PEGDE crosslinked
○  HRP — periodate/Schiff base crosslinked
△  HRP — PEGDE crosslinked

SOYBEAN PEROXIDASE ELECTROCHEMICAL SENSOR

FIELD OF THE INVENTION

This invention relates to biosensors for the electrochemical detection of hydrogen peroxide. More particularly, this invention relates to an electrochemical sensor containing immobilized thermostable peroxidase, e.g., soybean peroxidase, the sensor having sustained sensitivity at temperatures of 37° C. and higher.

BACKGROUND OF THE INVENTION

Electrochemical, particularly amperometric, chronoamperometric, and chronocoulometric sensors of hydrogen peroxide are used in the assay of biochemicals including glucose, lactate, and cholesterol, as well as in the detection and assay of immunoreagents, in nucleic acid sensors, and in sensors detecting other affinity reactions. Hydrogen peroxide biosensors are also used to monitor biochemicals in vivo, such as glucose and lactate. In vivo monitoring of glucose is relevant to the management of diabetes mellitus. Monitoring of lactate is important to the confirmation of hypoxia or ischemia.

Glucose can be monitored subcutaneously or transcutaneously, i.e., by transporting glucose across the skin and measuring its concentration. A general method for assaying glucose involves reacting glucose in a test sample with molecular oxygen in the presence of excess glucose oxidase. The reaction produces hydrogen peroxide and gluconolactone, and the hydrogen peroxide is sensed with a hydrogen peroxide sensor. For measuring lactate or cholesterol, hydrogen peroxide is similarly produced in the respective presence of lactate oxidase or cholesterol oxidase.

Hydrogen peroxide is electrochemically detected by its electrooxidation on a platinum or other relatively inert platinum-group metal electrode. Platinum electrodes, however, become fouled in biological fluids, limiting their use. Unless the surface of the platinum electrode is cleaned or reconditioned periodically, e.g., by chemical cleaning or electrochemical oxidation and reduction, the potential dependence of the rate of electrooxidation of hydrogen peroxide, and thus the sensitivity of the platinum-based detector, changes.

The fouling problem was previously addressed through use of non-corroding metal or carbon electrodes coated with films comprising peroxidase, e.g., horseradish peroxidase. In such sensors, the peroxidase was oxidized by hydrogen peroxide, and then electroreduced either directly or through a process involving a diffusing electron-relaying species.

Amperometric enzyme electrodes containing peroxidase for hydrogen peroxide detection have been described. In these prior art sensors, peroxidase is obtained from horseradish, Arthromyces ramosus, and bovine milk. See, for example, Kulys and Schmid, 1990, *Bioelectrodchem. Bioenerg.* 24:305–311; Wang et al., 1991, *Anal. Chim. Acta*, 254:81–88; and Gorton et al., 1991, *Anal. Chim. Acta* 250:203–248; and Paddock et. al., 1989, *J. Electroanal. Chem. Interfacial Electrochem.* 260:487–494. However, these sensors could not be operated for prolonged periods of time at 37° C. or above without significant loss of sensitivity.

Prior art peroxidase electrodes also included those based on "wiring" enzymes to electrodes through electron-conducting hydrogels. Because the enzyme "wired" hydrogels are highly permeable to hydrogen peroxide and conduct electrons, covalent bonding of the peroxidase to the cross-linked polymer network yielded hydrogen peroxide sensors with high sensitivity. See, for example, Gregg and Heller, U.S. Pat. No. 5,320,725; Vreeke and Heller, 1994, In: *Diagnostic Biosensor Polymers;* Usmani and Akmal, eds., ACS Symposium Series 556; and Vreeke et al., 1992, *Anal. Chem.* 64:3084–3090 which are hereby incorporated by reference. The current of these "wired" peroxidase sensors is mass transport controlled over a broad concentration range and thus varies linearly with the hydrogen peroxide concentration. In the "wired" peroxidase sensors, the peroxidase is covalently bound to a redox polymer network of an electron-conducting hydrogel coating the electrode. The sensitivity of these sensors is as high as 1 $Acm^{-2}M^{-1}$. These sensors also have less noise than platinum electrodes at equal current density, and, unlike platinum electrodes, they are not fouled in biological solutions.

Although the operational life of the "wired" peroxidase sensor is sufficiently long to be adequate for most applications at 25° C., its operational life is severely reduced at temperatures at or above 37° C. For example, when used continuously for several days at or near the temperature of the human body, 37° C., the wired peroxidase sensor lost its sensitivity. In addition, because the sensor rapidly lost its sensitivity at temperatures above 37° C., it could not be used for prolonged periods in bioreactors or bioanalytical systems operating at or above 37° C. Furthermore, nucleic acid-sensing by electrochemical processes which rely on denaturing paired nucleic acid strands at temperatures in excess of 50° C. requires thermostable electrochemical devices.

Many attempts have been made to improve the operational stability of enzyme biosensors. Enzyme electrodes designed with an excess of enzyme and a membrane to reduce the flux of substrate have been used to improve the operational stability of enzyme electrodes. See, for example, the Instruction Manual for YSI Model 23A and 23 AM glucose analyzer produced by Yellow Springs Instruments, Inc., Yellow Springs, Calif., and Alvarez-Icaza and Bilitewski, 1993, *Anal. Chem.* 65:525A–533A. These sensors maintain their performance specifications even after most of their enzyme has become inactive, because residual enzyme suffices to completely convert the restricted substrate flux.

Other stabilization methods focused on slowing the inactivation of the enzyme. Researchers who assumed that enzyme inactivation resulted from an irreversible change in protein folding, modified the protein surface or fixed its structure by cross-linking for better stability. See, for example, Chien et al., 1994, *Biotechnol. Appl. Biochem;* 19:51–60; Asther and Muenier, 1993, *App. Biochem. Biotechnol.* 38:57–67; and Mosbach, K., Ed., 1988, *Methods in Enzymology,* Academic Press, San Diego, Vol 135–137.

Thermostability was improved by covalently bonding enzyme in a phospholipid modified surface that resembled the enzyme's natural, membrane environment. See, for example, Kallury et al., 1992, *Anal. Chem.,* 64:1062–1068 and 1993, 65:2459–2467. However, the lipids and the substrates to which the lipids were bound were insulating. Therefore these lipid-stabilized systems could not be useful as thermostable electrochemical sensors. Enhancement of sensor thermostability using enzymes isolated from thermophilic organisms has been considered theoretically, but these enzymes are unavailable in the needed quantity and/or do not have the required activity. Thermostable biosensors remain commercially unavailable. Moreover, those thermostable enzymes that were proposed for use in biosensors were not enzymes that could be used in the assay of hydrogen peroxide.

Soybean peroxidase has recently become commercially available. While the manufacturer claims that the enzyme is stable at 80° C. for 12 hours, its stability and sensitivity in electrochemical reactions are unknown. The enzyme has been disclosed as useful in biochemical and immunological assays in which horseradish peroxidase is useful (U.S. Pat. No. 5,278,046). The utility of this enzyme in electrochemical applications is unknown.

Thus, despite advances in operational stability of enzyme electrodes, stable, sensitive electrodes for the detection of hydrogen peroxide are not available. It would be highly desirable to provide a stable and sensitive biosensor for the detection of hydrogen peroxide which is thermostable, e.g., able to withstand operation at temperatures of 37° C. and higher for sustained periods of time.

SUMMARY OF THE INVENTION

Remarkably thermostable biosensors for the detection of hydrogen peroxide in electrochemical assays are provided by the use of a thermostable peroxidase, e.g., peroxidase isolated from soybean. The preferred sensors of the invention are produced by immobilizing a thermostable peroxidase together with nonleachable redox compounds in a hydrogel-forming composition. (A hydrogel is a composition that swells in an aqueous solution, increasing its volume or weight by at least a factor of 1.2, i.e., adding at least 20% to its weight or volume when hydrated.) Most preferably, soybean peroxidase and a redox polymer are cross-linked on the surface of conductive carbon, tin oxide, indium oxide, gold or palladium to form a thermostable, non-fouling, hydrogen peroxide sensor.

In an alternative embodiment of the invention, thermostable peroxidase is bound to a nucleic acid probe and used in a method of electrochemical sensing of a specific nucleotide sequence. A nucleic acid sample to be probed is adsorbed or bound directly or through a water soluble redox polymer onto an electrode. The nucleic acid or the nucleic acid-redox polymer film is not leached off the electrode, and its constituents are not leached from the film in physiological salt solutions in the 5–8 pH range. The nucleic acid on the electrode is denatured, or melted to separate hybridized strands. The electrode with single-stranded nucleic acid is then permitted to hybridize with a nucleic acid or oligonucleotide probe containing bound thermostable peroxidase. Complementary binding or hybridization of the probe to the nucleic acid-electrode is signalled by a current resulting from the electroreduction of added hydrogen peroxide.

DETAILED DESCRIPTION OF THE INVENTION

Figure 1:
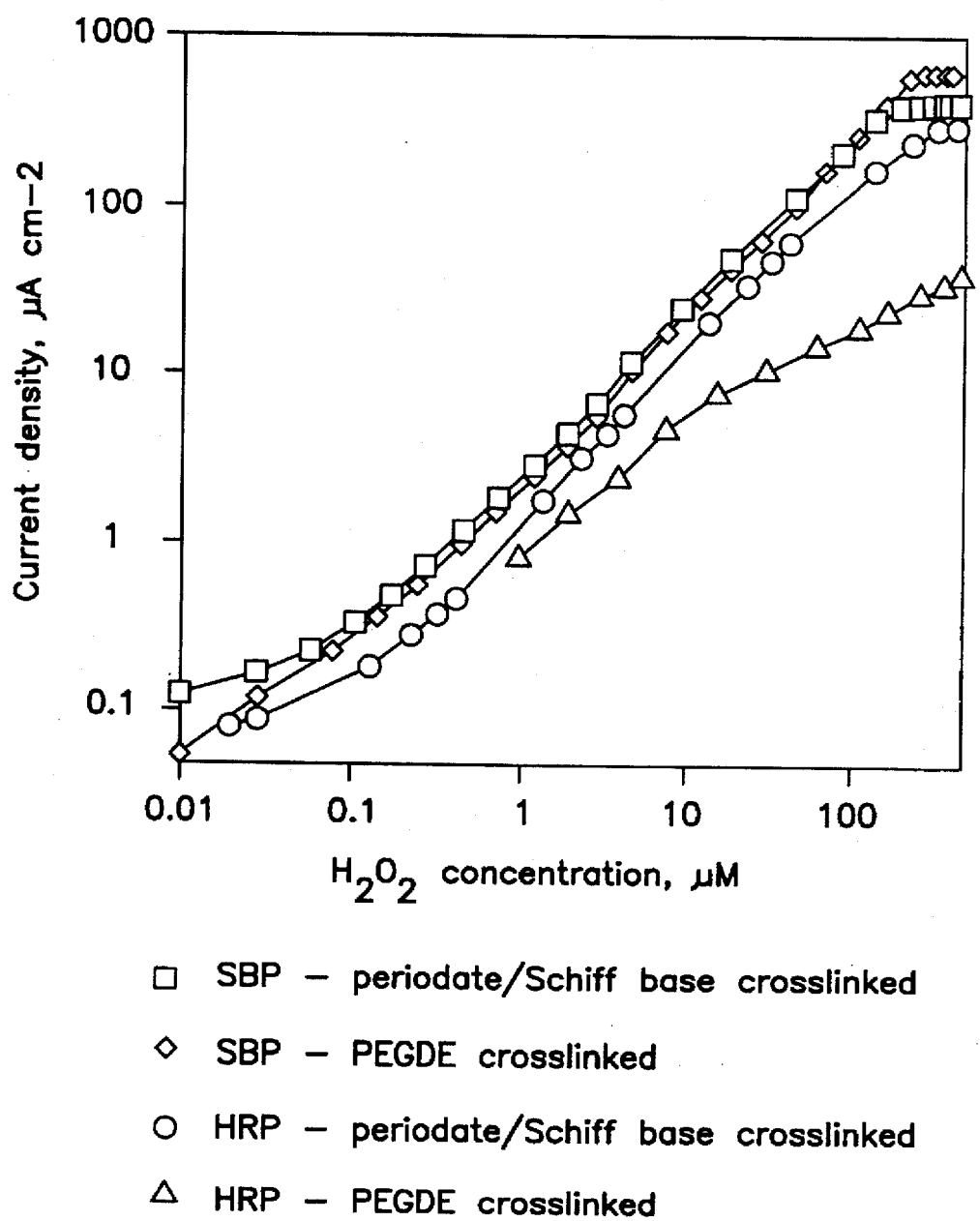
FIG. 1 is a graphic representation of data generated in Example 1, comparing horseradish peroxidase-based sensors with soybean peroxidase-based sensors.

The hydrogen peroxide sensors of the present invention are thermostable electrochemical sensors, suitable for use e.g., on the skin and in vivo, as well as in bioanalytical flow systems. The inventive sensors have no leachable components. The inventive sensors are generally formed by immobilizing a thermostable peroxidase together with oxidizable-reducible (redox) compounds on a non-corroding electrode. The sensor operates in biological fluids and tissues, at temperatures near 37° C. or in excess of 37° C. for sustained periods of time, e.g., days, without significant loss of sensitivity, e.g., less than 5%.

Electrochemical sensors can be amperometric, measuring current, potentiometric, measuring potential, or coulometric, measuring charge passed. Measurement can be continuous, intermittent, or in a time window between t1 and t2.

THERMOSTABLE PEROXIDASE

Thermostable peroxidase is commercially available, e.g., soybean peroxidase, from Enzymol International, Inc. (Columbus, Ohio). To be useful in the electrochemical sensors of the invention, a thermostable peroxidase must be stable at temperatures of 37° C. and higher, and is preferably stable at 50° C. and higher, with stability defined as less than 5% loss of enzyme activity per hour of continuous use in the presence of redox compounds. Most preferably, the thermostable peroxidase is one which at 55° C. loses less than 2% of its activity per hour when dissolved in an aqueous solution containing about 0.1M NaCl and $10^{-4}$M hydrogen peroxide at pH 7 when the enzyme is oxidized by hydrogen peroxide of $10^{-4}$M concentration or less and is electroreduced through a reaction involving the redox compound.

The thermostable peroxidase may be naturally-derived or recombinant. Preferably, the peroxidase includes oligosaccharide side chains which are retained on the molecule after its immobilization on the electrode.

CONDUCTING NON-CORRODING ELECTRODE

Thermostable, electrochemical sensors for the detection of hydrogen peroxide are preferably formed on the surface of an electron-conducting, non-corroding substrate such as gold, palladium, tin oxide, indium oxide or carbon. The carbon can be vitreous of graphitic. The peroxidase may be immobilized on the substrate by methods generally known in the art, including coating the conducting substrate with a polymeric film containing the enzyme and/or covalently bonding or cross-linking the enzyme to the electrode and/or polymeric film. Preferably, the thermostable peroxidase is coimmobilized with a water-soluble redox polymer, through cross-linking with a water-soluble cross-linker, onto the surface of the electrode.

POLYMERIC FILM

The hydrogen peroxide sensors of the invention are preferably formed by immobilizing thermostable peroxidase in either (1) a hydrogel made by crosslinking of a water-soluble polymer that is not leached off the surface of the electrode once attached or adsorbed, or (2) a water-insoluble polymer that swells in water, and coating the polymer-peroxidase composition onto a non-corroding electrode. After attachment to the electrode, the water-soluble polymer is not leached off the electrode in aqueous solution of NaCl, e.g., 0.1 to 1.0M, pH 5 to pH 8. After equilibration with water, the water-insoluble polymer contains not less than 20% water by weight. An example of a water-soluble redox polymer that is crosslinked to form a useful hydrogel is the polymer of Gregg & Heller, 1991, *J. Phys. Chem.*, 95:5970 which is hereby incorporated by reference for all purposes. Other useful polymers are redox polymers, containing, when dry, between 0.1 and 3.0 moles per kilogram of non-leachable redox centers.

Non-leachable redox centers are those which are not leached by water, plasma, serum, blood or physiological buffer solutions under standard use and operating conditions. Useful redox centers have a redox potential between about 450 mV and −200 mV versus standard calomel electrode (SCE). Preferred non-leachable redox centers are stable complexes of metals, particularly of group VIII metals such as osmium or ruthenium, produced as described in Gregg & Heller, 1991, discussed above.

SECOND ENZYME LAYER

Preferably, the hydrogen peroxide sensor also contains a second enzyme immobilized in or on the layer containing the soybean peroxidase. The second enzyme is one that catalyzes a reaction in which hydrogen peroxide is produced, e.g., glucose oxidase. This second enzyme may be coimmobilized by cross-linking with a stabilizing polymer such as polyethyleneimine or poly-N-vinylimidazole, or with a polyanion such as NAFION that may exclude electrooxidizable anionic interferant. The second enzyme may be coimmobilized in the redox polymer containing the peroxidase, or preferably is contained in a separate membrane or second polymeric layer.

Preferred second enzymes are glucose oxidase, lactate oxidase, and cholesterol oxidase. The second enzyme is present in great excess, such that when about 90% of the second enzyme's initial activity is lost, sufficient enzymatic activity is retained to catalyze the conversion of at least 90% of the substrate reaching the second enzyme-containing layer through its reaction with oxygen, and thereby producing oxidized substrate and hydrogen peroxide, sensed as described in Yang et. al., 1995, *Anal. Chem.*, 67:1326; and in Vreeke and Heller, 1994, In: *Diagnostic Biosensor Polymers*, Usmani and Akmal, Eds., ACS Symposium Series 556:180–193. Because of the great excess of the second enzyme, usually an oxidase, the electrode retains its sensitivity after the oxidase is thermally deactivated. In the prior art sensors, although the oxidase retained sufficient sensitivity, the unstable "wired" peroxidase did not. The present invention solves this problem by providing a thermostable peroxidase which retains its sensitivity under conditions which would deactivate previously known peroxidases.

BIOCOMPATIBLE OVERCOATING

The sensors of the present invention are particularly suited for sensitive monitoring of biochemical analytes in vivo and in flow systems when the latter operate near 37° C. or above. Factors contributing to this utility include the improved stability of the sensor, particularly improved thermostability. The inventive sensor also has no leachable components to cause concern, when used in the body, and does not deplete its redox compound in a flow system.

For in vivo use, the sensor is preferably coated with a biocompatible film that is highly permeable to the substrate converted in the reaction catalyzed by the second enzyme, usually an oxidase. This biocompatible film is placed on the solution side of the sensor.

In general, the biocompatable overcoating is formed of a hydrogel, e.g., a polymeric composition which contains more than 20% by weight of water when in equilibrium with a physiological environment such as living tissue or blood. An example is cross-linked poly(ethylene oxide), e.g., poly (ethylene oxide) tetraacrylate. The polymeric compositions must be non-toxic and compatible with living systems.

ELECTROCHEMICAL ASSAY OF HYDROGEN PEROXIDE

In the method of the present invention, hydrogen peroxide is assayed using an electrode containing immobilized, thermostable peroxidase. The thermostable peroxidase is preferably coimmobilized with a non-leachable redox compound onto a non-corroding, electron-conducting substrate, e.g., via a hydrogel. In the preferred embodiment, the thermostable peroxidase is "wired" to the electrode via the immobilized, non-leachable redox polymer that is crosslinked to form a redox hydrogel.

The hydrogen peroxide sensors of the present invention operate in biological fluids at high temperatures, which would inactivate previously available peroxidase enzymes, e.g., those derived from horseradish. The inventive sensors operate at temperatures in excess of 37° C., and even in excess of 50° C., with less than 2% loss in sensitivity per hour of continuous operation. They may be sterilized for use in vivo, and tolerate high temperatures in bioreactors in flow analyzers.

By using an electron-conducting redox hydrogel with a thermostable peroxidase, a remarkably stable hydrogen peroxide sensor, having no leachable components, and operable at high temperatures, e.g., 65° C., can be made. Such a thermostable sensor competes in both sensitivity and stability with platinum and other group VIII metal electrodes on which hydrogen peroxide is now assayed through its electrooxidation. The inventive sensors have unique advantages over the platinum type, however, including being less prone to fouling.

ELECTROCHEMICAL NUCLEIC ACID ASSAY

In an alternative preferred embodiment, thermostable peroxidase is used in an electrochemical assay of a specific nucleotide sequence. Thermostable peroxidase is bound to a nucleic acid probe. A nucleic acid sample to be probed is irreversibly adsorbed, bound, or cross-linked onto a non-corroding electrode as described above, preferably via a non-leaching water-soluble polymer, or a swellable, water-insoluble polymer. The polymer-attached nucleic acid is not leachable from the electrode, and, as described above, the polymer also contains immobilized, nonleachable, redox centers.

The nucleic acid-electrode either contains single-stranded nucleic acid or is subjected to denaturing conditions, e.g., heat in excess of 50° C., in order to cause separation of hybridized nucleic acid strands. After washing, the single-stranded nucleic acid-electrode is reacted under hybridization conditions with the nucleic acid-thermostable peroxidase probe. Hybridization conditions appropriate for anaylsis of a particular nucleic acid pairing will vary with the nucleic acid molecules involved. This variation is understood by one of skill in the art, and the appropriate conditions for the desired analysis can be calculated by known methods. See, for example, discussion of hybridization kinetics in a general biochemistry or molecular biology textbook, for example, Darnell et.al., eds., *Molecular Cell Biology*, Scientific American Books, Inc., New York, 1986, including the hybridization discussion beginning on page 237. Hybridization of the probe to the nucleic acid-electrode is signaled by a current resulting from electroreduction of added hydrogen peroxide.

After detection, the peroxidase-labeled hybrid is melted or denatured and the strand containing the thermostable peroxidase is washed away from the nucleic acid-electrode, disrupting the electrical contact between the enzyme and the electrode. The absence of an electrocatalytic peroxide reduction current in the denatured condition confirms any prior hybridization results.

Denaturing by melting, i.e., unpairing of strands by raising the temperature of the nucleic acid solution, reduces the electroreduction current of hydrogen peroxide. Consequently, one can determine not only the presence or absence of hybridization, but one can also discriminate between hybrids that denature to a different extent at differing temperatures by the method of the invention. This capability of the electrochemical sensing method of the invention is particularly useful in determining the sequence of a particular nucleic acid, and in automated electrochemical methods for rapid nucleic acid sequencing.

The invention will be further characterized by the following examples. These examples are not meant to limit the scope of the invention which has been fully set forth in the foregoing description. Variations within the concepts of the invention are apparent to those skilled in the art.

EXAMPLES

Example 1

Comparison of Peroxidase from Horseradish and Soybean in Hydrogen Peroxide Sensors Peroxidase enzyme from horseradish (HRP), E.C. 1.11.1.7 (Sigma P-8375 type VI-A, 1380 ABTS units/mg) was compared with peroxidase enzyme from soybean (SBP) (Enzymol Int'l.,Inc., HP grade 130 pyrogallo units/mg).

Redox polymer (POs-EA) was synthesized by partially complexing the pyridine nitrogen of poly(4-vinylpyridine) with $Os(bpy)_2Cl^{+/2+}$, then partially quaternizing the product with 2-bromoethylamine as described in Gregg and Heller, 1991, *J. Phys. Chem.* 95:5970. The osmium-containing redox centers of POs-EA provide for electron conduction between the glassy carbon electrode and peroxidase heme centers, and the pyridinium-N-ethylamine functions enhance hydration and provide primary amines for cross-linking. The ratio of unmodified pyridines to osmium complexed pyridines to bromoethylamine quaternized pyridines was 1:3.35:0.6.

Vitreous carbon rotating disk electrodes (3 mm) were built as described in Vreeke et.al., 1992, *Anal. Chem.* 64:3084–3090. The electrodes were polished successively with 5 μm, 1 μm, and 0.3 μm alumina and thorough sonication after each polishing step. A Pine Instruments rotator AFMSRX coupled with an ACMDI 1906C shaft was used for creating uniform mass transfer.

A hydrogen peroxide sensing layer comprising the peroxidase enzyme, HRP or SBP, was applied to the 3 mm vitreous carbon electrode. The enzyme and redox polymer were cross-linked either (1) by the diepoxide poly(ethylene glycol 400 diglycidyl ether) (PEGDGE) (technical grade, Polysciences #08210) or (2) by partial periodate ($IO_4^-$) oxidation of the peroxidase oligosaccharide to aldehydes and Schiff base formation, with amines of the redox polymer.

The diepoxide cross-linked films were made by applying 1.3 ul of a solution containing 5 mg/ml PVP-$NH_2$-Os, 5 mg/ml HRP or SBP, and 2.5 mg/ml PEGDGE mixed in a 3:2:1 ratio. Cross-linking by Schiff base formation followed the oxidation of part of the enzymes' oligosaccharides by $NaIO_4$. In this procedure, HRP or SBP (2 mg) was dissolved in 100 ml 0.1M sodium bicarbonate. After adding 50 ml of 12 mg/ml $NaIO_4$, the enzyme solution was incubated in the dark for 2 hours. A 5 mg/ml solution of POs-EA was then mixed with the enzyme solution at a 10:3 ratio. A volume of 2.3 ml of the POs-EA-enzyme solution was then applied to the polished vitreous carbon surface. The films were allowed to dry and cure for a minimum of 24 hours at room temperature prior to use.

Electrochemical measurements were performed in a modified Dulbecco's buffer (PBS), pH 7.4, in a standard three electrode cell with a platinum foil counter and a Ag/AgCl Bioanalytical Systems reference electrode. All potentials were reported relative to that of the Ag/AgCl reference electrode. An EG&G potentiostat/galvanostat model 173 or Bioanalytical Systems CV-1B was used to take the electrochemical measurements. The temperature was controlled by using an EG&G electrochemical cell and a model 9101 circulating water bath (Fisher Scientific). The volume of the electrochemical cell was 125 ml. Aliquots of concentrated stock solutions of hydrogen peroxide were added so as to hold the test solution volume reasonably constant.

The concentration of stock hydrogen peroxide solution (30%, Aldrich) was verified by measuring its density. Solutions of hydrogen peroxide for use were prepared fresh daily. Hydrogen peroxide sensor stability measurements were performed at 0.1 mM hydrogen peroxide concentration. Because the hydrogen peroxide solutions are inherently unstable and hydrogen peroxide was electroreduced at the electrodes, the solutions were refreshed periodically, particularly when the tests were prolonged or at elevated temperatures.

The electrodes were optimized for sensitivity by varying first the enzyme:redox polymer ratio, then varying the loading, i.e., the total amount of solids on the electrode surface, both at 25° C. The sensitivities and the dynamic ranges of "wired" HRP and SBP electrodes are compared in FIG. 1. Optimized sensors made by the two types of cross-linking methods are also compared in FIG. 1.

The data shown in FIG. 1 indicate that while cross-linking by $NaIO_4$ oxidation and Schiff base formation yielded more sensitive sensors with HRP, as compared to HRP sensors crosslinked with the diepoxide, there was little, if any, difference in the sensitivities of SBP sensors made by these methods.

As shown in Table 1, the HRP-based electrode cross-linked by the oxidation and Schiff base method was stable in continuous operation at 25° C., losing only about 0.1% of its activity per hour of continuous operation at 0.0 V. However, when the same electrode was tested at 45° C., it lost more than 10% of its sensitivity per operating hour.

The stability of the HRP-based electrode cross-linked by diepoxide (PEGDGE) cross-linking was poorer at 25° C. than the stability of the HRP-based electrode made by periodate/Schiff base cross-linking. This sensor lost 0.9% of its sensitivity per hour of operation at 25° C. Nevertheless, at 45° C., this HRP-based sensor lost only 5.6% of its sensitivity per hour of operation.

The improved operational stability of the PEGDGE cross-linked SBP sensor is compared with that of the PEGDGE cross-linked HRP sensor in Table 1. The SBP-based sensor was remarkably stable at high temperatures, losing only 0.15% of its sensitivity per hour while operating at 55° C. and only 1.7% per hour at 65° C. This sensor had a four hour operational half-life at 75° C. The stability of the SRP sensor is in contrast to the HRP sensor made by the same PEGDGE crosslinking method, which lost 10% of its activity per hour at 55° C. and 50% per hour at 65° C.

Although the sensitivity of the SBP-based hydrogen peroxide sensor was temperature-dependent, the activation energy was moderate. The current increased only by 30% when the temperature was raised by 20° C. from 5° C. to 25° C., and only doubled when the temperature was raised by 50° C. from 25° C. to 75° C.

TABLE I

| Electrode/cross-linker | Rate of Loss in Electrode Sensitivity at Various Temperatures (% per hour)* | | | | |
|---|---|---|---|---|---|
| | 25° C. | 45° C. | 55° C. | 65° C. | 75° C. |
| HRP/IO$_4$ Schiff base | 0.1% | 10% | — | — | — |
| HRP/PEGDGE | 0.9% | 5.6% | 9.9% | 50% | >50% |
| SBP/PEGDGE | 0.1% | 0.05% | 0.15% | 1.7% | 13% |

*Measurement conditions: 100 uM H$_2$O$_2$ in PBS, pH7.4, 1000 RPM, 0mV vs Ag/AgCl.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. An electrochemical hydrogen peroxide sensor comprising:

a non-corroding electrode; and thermostable soybean peroxidase immobilized on the non-corroding electrode and electrically connected to the non-corroding electrode, the sensor having no leachable components, and being capable of operation at temperatures of 37° C. or higher with less than 2% loss of sensitivity per hour of continuous operation.

2. The hydrogen peroxide sensor of claim 1, wherein the peroxidase is immobilized on the electrode via a redox hydrogel.

3. The hydrogen peroxide sensor of claim 1, wherein the peroxidase is cross-linked to a redox polymer.

4. The hydrogen peroxide sensor of claim 1, wherein the peroxidase is covalently bound to a nucleic acid or to an oligonucleotide.

5. The hydrogen peroxide sensor of claim 1, wherein the peroxidase is a recombinant protein.

6. The hydrogen peroxide sensor of claim 1, further comprising:

an enzyme which catalyzes the production of hydrogen peroxide.

7. The hydrogen peroxide sensor of claim 6, wherein said enzyme is selected from the group comprising glucose oxidase, lactate oxidase, and cholesterol oxidase.

8. The hydrogen peroxide sensor of claim 1, further comprising:

a biocompatible polymeric coating covering at least a portion of the electrode, the coating being permeable to hydrogen peroxide.

9. The hydrogen peroxide sensor of claim 1, capable of operation at temperatures of at least 50° C. with less than 5% loss in sensitivity per hour of continuous operation.

10. A method for the electrochemical analysis of hydrogen peroxide, said method comprising the steps of:

generating an electrical signal by an electrode in the presence of hydrogen peroxide, the electrode comprising a thermostable soybean peroxidase coimmobilized with a non-leachable redox compound on a non-corroding electrode; and, correlating the generated electrical signal with the presence of hydrogen peroxide in the sample.

11. A method for continuous measurement of analyte, comprising the steps of:

placing a sensor on or in a body fluid or tissue, the sensor comprising a thermostable soybean peroxidase electrically connected to a non-corroding electrode and co-immobilized with a non-leachable redox compound onto the electrode and a second enzyme immobilized on the electrode, the second enzyme catalyzing a reaction which generates hydrogen peroxide in the presence of a specified analyte, and correlating an electrical signal generated by the electrode with the amount of analyte present in the body fluid or tissue.

12. A method for monitoring glucose concentration in vivo, comprising the steps of:

placing in a subject's body fluid or tissue a sensor comprising a thermostable soybean peroxidase electrically connected to a non-corroding electrode and co-immobilized with a non-leachable redox compound onto the electrode, and glucose oxidase immobilized onto the electrode; and correlating an electrical signal generated by the electrode with the amount of glucose present in the body fluid or tissue.

13. A method for monitoring the concentration of an analyte in a bioreactor operating at temperatures of 37° C. or greater, comprising the steps of:

placing in the bioreactor, in contact with the bioreactor's contents, a sensor comprising a thermostable soybean peroxidase coimmobilized with a non-leachable redox compound onto a non-corroding electrode; and correlating an electrical signal generated by the electrode with the amount of analyte in the bioreactor.

14. A method for detecting hybridization of a nucleic acid probe to a sample nucleic acid, comprising the steps of:

immobilizing a sample nucleic acid on a non-corroding electrode;

incubating the sample nucleic acid-electrode with a nucleic acid probe having bound thereto a thermostable soybean peroxidase, under hybridization conditions; and correlating an electrical signal produced by the electrode in the presence of added hydrogen peroxide with hybridization of the nucleic acid probe to the sample nucleic acid.

15. The method of claim 14, further comprising the step of disrupting electrical contact between the electrode and the thermostable peroxidase-nucleic acid probe.

16. The method of claim 15, wherein said disrupting is denaturing the hybridization product of the sample nucleic acid electrode and the thermostable peroxidase-nucleic acid probe.

17. The method of claim 16, wherein said denaturing is caused by altering the conditions under which the sample nucleic acid electrode and the thermostable peroxidase-nucleic acid probe are incubated.

18. A method for analyzing the composition of a sample nucleic sequence comprising the steps of:

immobilizing a sample nucleic acid on a non-corroding electrode;

incubating the sample nucleic acid-electrode with a nucleic acid probe having bound thereto a thermostable soybean peroxidase, under hybridization conditions; and correlating an electrical signal produced by the electrode in the presence of added hydrogen peroxide with hybridization of the nucleic acid probe to the sample nucleic acid and to the composition of the sample nucleic acid sequence.

19. A method for analyzing the composition of a sample nucleic sequence comprising the steps of:

immobilizing a sample nucleic acid on a non-corroding electrode;

incubating the sample nucleic acid-electrode with a nucleic acid probe having bound thereto a thermostable soybean peroxidase, under varying hybridization conditions; and correlating changes in electrical signals produced by the electrode in the presence of added hydrogen peroxide under the varying hybridization conditions with variation in hybridization of the nucleic acid probe to the sample nucleic acid and to the composition of the sample nucleic acid sequence.

* * * * *

UNITED STATES PATENT AND TRADEMARK OFFICE
CERTIFICATE OF CORRECTION

PATENT NO. : 5,665,222

DATED : September 9, 1997

INVENTOR(S) : Heller et al.

It is certified that error appears in the above-identified patent and that said Letters Patent is hereby corrected as shown below:

In column 4, line 32: "of" should read --or--.

Signed and Sealed this

Seventh Day of April, 1998

*Attest:*

BRUCE LEHMAN

*Attesting Officer*     *Commissioner of Patents and Trademarks*